United States Patent [19]

Kosley, Jr. et al.

[11] Patent Number: 4,883,793

[45] Date of Patent: Nov. 28, 1989

[54] HYDRAZINOCARBONYLOXYLABDANES FOR TREATING CARDIAC FAILURE

[75] Inventors: Raymond W. Kosley, Jr., Bridgewater, N.J.; Gerard J. O'Malley, Newton, Pa.

[73] Assignee: Hoechst-Roussel Pharmaceuticals Inc., Somerville, N.J.

[21] Appl. No.: 191,457

[22] Filed: May 9, 1988

[51] Int. Cl.$^4$ .................. A61K 31/54; C07D 405/12
[52] U.S. Cl. .................. 514/228.2; 514/232.8; 514/337; 514/365; 514/374; 514/422; 514/432; 514/444; 514/455; 544/58.7; 544/150; 546/196; 546/269; 548/194; 548/215; 548/525; 549/28; 549/60; 549/358; 549/389
[58] Field of Search .................. 549/389, 358, 28, 60; 546/196, 187, 269; 544/79, 58.6, 58.7, 150; 514/455, 228.2, 232.8, 337, 365, 374, 422, 432, 444; 548/194, 215, 525

[56] References Cited

U.S. PATENT DOCUMENTS

| | | | |
|---|---|---|---|
| 3,631,039 | 12/1971 | Nutley et al. | 544/149 |
| 4,088,659 | 5/1978 | Bhat et al. | 549/389 |
| 4,118,508 | 10/1978 | Bhat et al. | 514/455 |
| 4,134,986 | 1/1979 | Bajwa et al. | 514/455 |
| 4,476,140 | 10/1984 | Sears et al. | 514/455 |
| 4,517,200 | 5/1985 | Kreutner et al. | 514/455 |
| 4,564,626 | 1/1986 | Krevtner et al. | 514/430 |
| 4,639,443 | 1/1987 | Kosley et al. | 514/222 |
| 4,639,446 | 1/1987 | Kosley et al. | 514/222 |
| 4,666,904 | 5/1987 | Kosley et al. | 514/222 |
| 4,672,115 | 6/1987 | Kosley et al. | 544/58.2 |
| 4,673,752 | 6/1987 | Kosley et al. | 549/389 |
| 4,677,103 | 6/1987 | Kosley et al. | 514/222 |

FOREIGN PATENT DOCUMENTS

| | | |
|---|---|---|
| 0126313 | 11/1984 | European Pat. Off. . |
| 0189801 | 8/1986 | European Pat. Off. . |
| 0192056 | 8/1986 | European Pat. Off. . |
| 0217372 | 4/1987 | European Pat. Off. . |
| 2654796 | 6/1978 | Fed. Rep. of Germany . |
| 3346869 | 7/1984 | Fed. Rep. of Germany . |
| 3407514 | 9/1985 | Fed. Rep. of Germany . |
| 3502686 | 8/1986 | Fed. Rep. of Germany . |
| 3623300 | 1/1988 | Fed. Rep. of Germany . |
| 3637 | 8/1986 | PCT Int'l Appl. . |

OTHER PUBLICATIONS

I. Sutherland(Editor), *Comprehensive Organic Chemistry*, vol. 2, Pergamon Press, New York, 1979, pp. 34–38 and 1049–1051.
De Souza, N., et al., *Medicinal Research Reviews*, 3, 201(1983).
Bhat, S., et al., *J. Med. Chem.*, 26, 486(1983).
Seamon, K., et al., *J. Med. Chem.*, 26, 436(1983).
Bhat, S., et al., *Tett. Lett.*, No. 19, 1669(1977).
Bhat, S., et al., *J.C.S. Perkin I*, 767(1982).
Caprioli, J., et al., *Invest. Ophth. Vis. Sci.*, 25, 268(1984).
Caprioli, J., et al., *The Lancet*, 958(1983).
Seamon, K., et al., *Proc. Natl. Acad. Sci. USA*, 78(6), 3363(1981).
Seamon, K., et al., *J. Biol. Chem.*, 256(19), 9799(1981).
Takeda, J., et al., *J. Invest. Dermatol.*, 81, 235(1983).
Takeda, J., et al., *J. Invest. Dermatol.*, 81, 131(1983).
Iizuka, H., et al., *Biochem. Biophys. Acta*, 444, 685(1976).
Iizuka, M., et al., *Biochem. Biophys. Acta*, 437, 150(1976).
Voorhees, J., et al., *J. Invest. Dermatol.*, 59, 114(1972).
Halprin, K., et al., *J. Invest. Dermatol.*, 65, 170(1975).
Raab, W., *Int. J. Clin. Pharmacol. Ther. Toxicol.*, 18, 212(1980).
Cherill, R., et al., *Abstracts of Papers*, 192nd ACS Meeting, Medi, No. 48(9/1986).
Caprioli, J., et al., *Yale J. Biol. Med.*, 57, 283(1984).
Seamon, K., et al., *Trends Pharmacol. Sci.*, 48, 120(1983).
Seamon, K., et al., *J. Cyc. Nucleotide Res.*, 7, 201(1981).
Caprioli, J., et al., *Abstracts Assn. Res. Vis. Ophthalmol.*, p. 233, No. 5:15(1986).
Bartels, S., et al., *Current Eye Res.*, 6(2), 307(1987).
Seamon, K., et al., in *Advances in Cyclic Nucleotide and Protein Phosphorylation Reasearch*, vol. 20, Greengard, P., et al. (editors), Raven Press, NY, 1986, pp. 1–150.
Bartels, S., et al., *Current Eye Res.*, 2, 673(1982/1983).
Laurenza, A., et al., *Molec. Pharmacol.*, 32, 133(1987).
Calbiochem Ⓡ Biochemical/Immunochemical Catalog, 1988, Non Product Supp., p. 18, 1987 catalog, p. 102. *Biologics*, 13(4), 10/1987.
March, J., *Advanced Organic Chemistry*, McGraw Hill, New York, 1968, pp. 320–322, 338 and 339.

*Primary Examiner*—Richard A. Schwartz
*Attorney, Agent, or Firm*—Raymond R. Wittekind

[57] ABSTRACT

Novel hydrazinocarbonyloxylabdanes, intermediates and processes for the preparation thereof, and a method for treating cardiac failure utilizing compounds or compositions thereof are disclosed.

22 Claims, No Drawings

HYDRAZINOCARBONYLOXYLABDANES FOR TREATING CARDIAC FAILURE

The present invention relates to labdanes. More particularly, the present invention relates to hydrazinocarbonyloxylabdanes of the formula

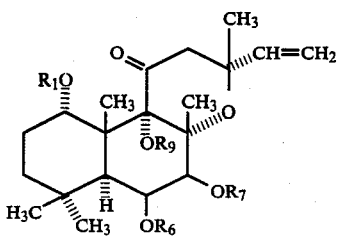

wherein:

(a) $R_1$ and $R_9$ are hydrogen;

(b) $R_1$ and $R_9$ taken together form a group of the formula CO, a group of the formula SO or a group of the formula $CHNR_2R_3$ wherein $R_2$ and $R_3$ are loweralkyl;

(c) $R_6$ and $R_7$ are independently hydrogen, a group of the formula $COR_{22}$ wherein $R_{22}$ is hydrogen or loweralkyl, or a group of the formula $CONR_4Z$ wherein $R_4$ is hydrogen or loweralkyl and Z is a group of the formula $NR_5R_8$ or a group of the formula $N=CR_{10}R_{11}$ wherein $R_5$ and $R_8$ are independently hydrogen, loweralkyl or a group of the formula $COR_{12}$ wherein $R_{12}$ is loweralkyl or a group of the formula $(CH_2)_nNR_{23}R_{24}$ wherein $R_{23}$ and $R_{24}$ are loweralkyl and n is an integer from 2 to 5; $R_5$ and $R_8$ taken together with the nitrogen atom to which they are attached form group of the formula

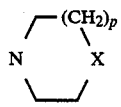

wherein X is O, S or a group of the formula $CHR_{13}$ wherein $R_{13}$ is hydrogen, loweralkyl or a group of the formula $OR_{14}$ wherein $R_{14}$ is hydrogen, loweralkyl or a group of the formula $COR_{15}$ wherein $R_{15}$ is loweralkyl and p is 0 or 1; $R_{10}$ is hydrogen, loweralkyl or hydroxyloweralkyl; $R_{11}$ is loweralkyl, loweralkenyl, hydroxyloweralkyl, a group of the formula

or a group of the formula

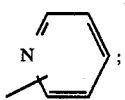

and $R_{10}$ and $R_{11}$ taken together with the carbon atom to which they are attached form a group of the formula

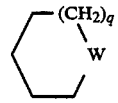

wherein W is O, S, a group of the formula $NR_{19}$ wherein $R_{19}$ is hydrogen or loweralkyl or a group of the formula $CHR_{16}$ wherein $R_{16}$ is hydrogen, loweralkyl or a group of the formula $OR_{17}$ wherein $R_{17}$ is hydrogen, loweralkyl or a group of the formula $COR_{18}$, wherein $R_{18}$ is loweralkyl and q is 0 or 1, with the proviso that either $R_6$ or $R_7$ is a group of the formula $CONR_4Z$ wherein $R_4$ and Z are as above; the optical and geometrical isomers thereof, or a pharmaceutically acceptable salt thereof, which are useful for treating cardiac failure.

Subgeneric to the hydrazinocarbonyloxylabdanes of the present invention are compounds of formula 1 wherein:

(a) $R_1$ and $R_9$ are hydrogen and Z is a group of the formula $NR_5R_8$;

(b) $R_1$ and $R_9$ taken together form a group of the formula $CHNR_2R_3$ and Z is $NR_5R_8$;

(c) $R_1$ and $R_9$ are hydrogen and Z is $N=CR_{10}R_{11}$;

(d) $R_1$ and $R_9$ taken together form a group of the formula $CHNR_2R_3$ and Z is $N=CR_{10}R_{11}$.

As used through the specification and appended claims, the term "alkyl" refers to a straight or branched chain hydrocarbon radical containing no unsaturation and having 1 to 8 carbon atoms. Examples of alkyl groups are methyl, ethyl, 1-propyl, 2-propyl, 2-methylpropyl, 1-pentyl, 2-pentyl, 3-hexyl, 4-heptyl, 2-octyl, and the like. The term "alkanol" refers to a compound formed by a combination of an alkyl group and a hydroxy radical. Exampes of alkanols are methanol, ethanol, 1- and 2-propanol, 1,2-dimethylethanol, hexanol, octanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid and the like. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl and the like. The term "lower" as applied to any of the aforementioned groups refers to a group having a carbon skeleton containing up to and including 6 carbon atoms.

In the formulas presented herein the various substitutents are illustrated as jointed to the labdane nucleus by one of two notations: a solid line (  ) indicating a substituent which is in the β-orientation (i.e., above the plane of the molecule) and a broken line ( - - - - - ) indicating a substituent which is in the α-orientation (i.e., below the plane of the molecule). The formulas have all been drawn to show the compounds in their absolute stereochemical configuration. Inasmuch as the starting materials having a labdane nucleus are naturally occurring or are derived from naturally occurring materials, they, as well as the final products, have a labdane nucleus existing in the single absolute configuration depicted herein. The processes of the present invention, however, are intended to apply as well to the synthesis of labdanes of the racemic series.

In addition to the optical centers of the labdane nucleus, the substituents thereon may also contain chiral centers contributing to the optical properties of the compounds of the present invention and providing a means for the resolution thereof by conventional methods, for example, by the use of optically active acids. The present invention comprehends all optical isomers and racemic forms of the compounds of the present invention, where such compounds have chiral centers in addition to those of the labdane nucleus.

The novel hydrazinocarbonyloxylabdanes of the present invention are synthesized by the processes illustrated in Reaction Schemes A and B.

To prepare a hydrazinocarbonyloxylabdane of formula 4, a $1\alpha,6\beta,7\beta,9\alpha$-tetrahydroxylabdane-$\alpha,9\alpha$-dialkylformamide acetal 2 ($R_1$ and $R_9$ taken together form a group of the formula $CHNR_2R_3$), the preparation of which is described in U.S. Pat. No. 4,639,443, granted Jan. 27, 1987, is acylated to a $7\beta$-hydrzinocarbonyloxylabdane-$1\alpha,9\alpha$-dialkylformamide acetal 3 ($R_1$ and $R_9$ are as above), which is hydrolyzed to 4. The acylation is accomplished by treating 2 with a 1,1'-carbonyldiimidazole 10

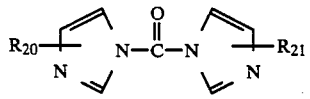

wherein $R_{20}$ and $R_{21}$ are hydrogen or loweralkyl followed by a hydrazine 11

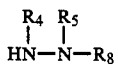

wherein $R_4$, $R_5$ and $R_8$ are as described hereinbefore in an ethereal solvent, a halocarbon or an alkyl alkanoate. Among ethereal solvents there may be mentioned tetrahydrofuran, dioxane, diethyl ether, di-2-propyl ether, 1,2-dimethoxyethane, 2-methoxyethyl ether, and the like. Among halocarbons there may be mentioned dichloromethane, trichloromethane, 1,2-dichloroethane, 1,1-dichloroethane, 1,1-dichloroethylene, 1,2-dichloroethylene and the like. Among alkyl alkanoates there may be mentioned methyl acetate, ethyl acetate, ethyl propionate, and the like. Tetrahydrofuran, dichloromethane, and ethyl acetate are the preferred solvents. The temperature at which the acylation is conducted is not narrowly critical. An acylation temperature within the range of about 10° to 50° C. is generally employed to assure a reasonable rate of reaction. A temperature of about 25° C. is preferred.

The hydrolysis of the acetal 3 ($R_1$ and $R_9$ are as above) to the triol 4 is accomplished in an aqueous alkanol such as aqueous methanol or ethanol at a temperature of about 10° C. to about 100° C., methanol and a temperature of about 45° to about 80° C. being preferred.

To construct an alkylidenylhydrazinocarbonyloxylabdane 6, a hydrazinocarbonyloxylabdane 4 wherein $R_5$ and $R_8$ are hydrogen is condensed with a carbonyl compound 12

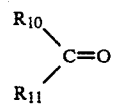

wherein $R_{10}$ and $R_{11}$ are as hereinbefore disclosed.

The condensation is effected by contacting 4 with a carbonyl compound 12 in the presence of a catalyst such as for example, silica gel preferably at about 25° C. or under conventional medium pressure liquid chromatography temperature conditions. Hydrocarbons, e.g., hexane, and alkyl alkanoates, e.g., ethyl acetate, as well as mixtures thereof may be employed in the condensation reaction as solvents or eluents.

Alternatively, a hydrazinocarbonyloxylabdane 4 is synthesized via an alkylidenylhydrazinocarbonyloxylabdane-dialkylformamide acetal 5 ($R_1$ and $R_9$ are as above) by acylation of a $1\alpha,6\beta,7\beta,9\alpha$-tetrahydroxylabdane-$1\alpha,9\alpha$-dialkylformamide acetal 2 ($R_1$ and $R_9$ are as above) with a hydrazine 11 wherein $R_4$ is hydrogen or alkyl and $R_5$ and $R_8$ are hydrogen in the presence of a 1,1'-carbonyldiimidazole 10 to provide a hydrazinocarbonyloxylabdane 3 which, without isolation, is condensed with a carbonyl compound 12 to afford an alkylidenylhydrazinocarbonyloxylabdane 5 ($R_1$ and $R_9$ are as above) and, in turn, hydrolyzed to a labdane 4. The acylation, condensation and hydrolysis processes are conducted under substantially the same conditions are hereinbeforedescribed for the corresponding transformation of 2 to 3, 4 to 6, and 3 to 4, respectively. Thus, for example, treatment of the dihydroxyacetal 2 ($R_1$ and $R_9$ taken together form a group of the formula $CHNR_2R_3$ wherein $R_2$ and $R_3$ are methyl) with 1,1'-carbonyldiimidazole 10 ($R_{20}$ and $R_{21}$ are hydrogen) in ethyl acetate a room temperature followed by 1-methylhydrazine 11 ($R_4$ is methyl and $R_5$ and $R_8$ are hydrogen), and, in turn, acetone 12 ($R_{10}$ and $R_{11}$ are methyl) in the presence of silica gel affords hydrazinocarbonyloxylabdane 4 ($R_5$ is methyl and $R_4$ and $R_8$ are hydrogen) via labdane 3 ($R_1$ and $R_9$ taken together form a group of the formula $CHNR_2R_3$ wherein $R_2$, $R_3$ and $R_4$ are as above and $R_{10}$ and $R_{11}$ are methyl).

To introduce a hydrazinocarbonyloxy function at the 6-position of the labdane nucleus, i.e., to prepare, for example, a compound of formula 8, a labdane-formamide acetal 2 ($R_1$ and $R_9$ taken together form a group of the formula $CHNR_2R_3$ where $R_2$ and $R_3$ are alkyl) is acylated with a 1,1-carbonyldiimidazole 10 in the presence of a hydrazine 11 to provide a $6\beta$-hydrazinocarbonyloxylabdane-dialkylformamide acetal 7 ($R_1$ and $R_9$ form a group of the formula $CHNR_2R_3$ wherein $R_2$ and $R_3$ are alkyl) which is hydrolyzed to a $6\beta$-hydrazinocarbonyloxy-$1\alpha,7\beta,9\alpha$-trihydroxylabdane 8. The acylation is carried out by treating 2 with 1,1-carbonyldiimidazole 10 in a halocarbon such as, e.g., dichloromethane, trichloromethane, tetrachloromethane, 1,1- or 1,2-dichloroethane, 1,1- or 1,2-dichloroethylene, and the like, an alkyl alkanoate such as, e.g., methyl acetate, ethyl acetate, ethyl propionate, and the like, or an ethereal solvent such as, e.g., tetrahydrofuran, dioxane, diethyl ether, and the like, in the presence of a tertiary amine such as, e.g., a trialkylamine (i.e., trimethylamine, triethylamine, tripropylamine, and the like, or a heteroromatic amine such as, e.g., pyridine, picoline, lutidine, collidine or the like), followed by a hydrazine 11 at an acylation temperature of from about 0° to the reflux temperature of the solvent system. The preferred solvent is a halocarbon, dichloromethane being most preferred. The preferred reaction temperature is about 25° C.

The hydrolysis is accomplshed by methods hereindescribed for the conversion of 3 to 4. Optionally, cosolvents such as alkanoic acids, for example, acetic acid, may be employed.

The hydrazinocarbonyloxylabdane 4 is further acylated at the hydrazino site by, for example, treatment with a carboxylic acid anhydride 14

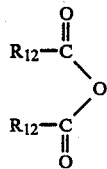

wherein $R_{12}$ is loweralkyl in halocarbon solvent such as those described for the conversion of 2 to 7 to provide 9, dichloromethane being preferred, at a temperature at which the acylation proceeds at a reasonable rate and which is compatible with the solvent system, an acylation temperature of about 25° C. being preferred.

To fabricate a hydrazinocarbonyloxylabdane-1,9-sulfite or 1,9-carbonate and an alkylidenylhydrazinocarbonyloxylabdane-1,9-sulfite or -1,9-carbonate of formulas 3 and 7, and 5, respectively, wherein $R_1$ and $R_9$ taken together form a group of the formula CO or a group of the formula SO, one may treat a $1\alpha,6\beta,7\beta,9\alpha$-tetrahydroxylabdane-1,9-sulfite or -1,9-carbonate, i.e., labdane 2 wherein $R_1$ and $R_9$ taken together form a group of the formula SO or CO with the appropriate reagents and under the appropriate conditions describedhereinbefore for the corresponding conversions of 2 to 3, 3 to 5, and 2 to 7.

A 6$\beta$-alkylidenylhydrazinocarbonyloxylabdane 13 wherein $R_{10}$ and $R_{11}$ are as hereinbeforedescribed may be synthesized from a 6$\beta$-hydrazinocarbonyloxylabdane 8 wherein $R_5$ and $R_8$ are hydrogen by the procedure described above for the conversion in the 7$\beta$-series, namely, the conversion of labdane 4 to 6.

To construct a 7$\beta$-alkanoyloxy-6$\beta$-hydrazinocarbonyloxylabdane 15 wherein $R_5$ and $R_8$ are alkyl and $R_{22}$ is hydrogen or alkyl, one may convert a 6$\beta$-hydrazinocarbonyloxylabdane-dialkylformamide acetal 7 ($R_1$ and $R_9$ form a group of the formula CHNR$_2$R$_3$ wherein $R_2$ and $R_3$ are alkyl, and $R_5$ and $R_8$ are as above) to a 7$\beta$-alkanoyloxy-6$\beta$-hydrazinocarbonyloxylabdane-dialkylformamide acetal 14 wherein $R_1$, $R_9$, $R_5$, $R_8$ are as above and $R_{22}$ is hydrogen or alkyl, which may then be hydrolyzed to a 7$\beta$-alkanoyloxylabdane 15 wherein $R_5$, $R_8$ and $R_{22}$ are as above. The conversion of 7 to 14 may be accomplished by treating a 7$\beta$-hydroxylabdane 7 with a carboxylic acid anhydride 26 wherein $R_{22}$ is loweralkyl or a mixed anhydride 27 wherein $R_{25}$ is loweralkyl

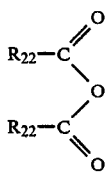

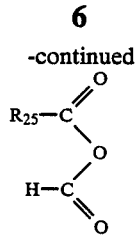

in the presence of a 4-substituted aminopyridine such as, for example, 4-N,N-dimethylaminopyridine, in a suitable solvent, if required. The hydrolysis of the dialkyformamide acetal function of a 6$\beta$-alkanoyloxylabdane 14 may be effected by in aqueous alkanol (e.g., aqueous methanol) by the hereinbeforedescribed method employed for the conversion of acetal 3 to triol 4. See Reaction Scheme C.

Similarly, a 7$\beta$-alkanoyloxy-6$\beta$-hydrazinocarbonyloxylabdane 18 wherein $R_{22}$ is hydrogen or alkyl may be prepared by protecting the amino function of the hydrazinocarbonyloxy group of labdane dialkylformamide acetal 7 wherein $R_1$ and $R_9$ form a group of the formula CHNR$_2$R$_3$ wherein $R_2$ and $R_3$ are alkyl and $R_{10}$ and $R_{11}$ are alkyl to provide a 6$\beta$-alkylidenylhydrazinocarbonyoxylabdane 16, acylating the 7$\beta$-hydroxyl group of 16 to afford 7$\beta$-alkanoyloxylabdane 17, and hydrolyzing the 1$\alpha$,9$\alpha$-dialkylformamide acetal and 6$\beta$-alkylidenylhydrazino groups of labdane 17 to provide a 7$\beta$-alkanoyloxy-6$\beta$-hydrazinocarbonyloxylbdane 18. The protection of hydrazinocarbonyloxy function of 7 may be performed by the process hereinbeforedescribed of the transformation of a 7$\beta$-hydrazinocarbonyloxylabdane 4 to 7$\beta$-alkylidenylhydrazinocarbonyloxylabdane 6. The acylation of the 7$\beta$-hydroxy group of the protected labdane 1$\alpha$,9$\alpha$-dialkylformamide acetal 16 wherein $R_1$ and $R_9$ are as above and $R_{10}$ and $R_{11}$ are alkyl may be conducted by contacting labdane 16 with an anhydride 26 wherein $R_{22}$ is as above or a mixed anhydride 27 wherein $R_{25}$ is loweralkyl in the presence of a dialkylaminopyridine, peferably 4-(N,N-dimethylamino)pyridine in an appropriate solvent, if necessary. The hydrolysis of the protecting groups of labdane 17 may be carried out by treating 17 with an aqueous alkanol, preferably aqueous methanol to provide 18. See Reaction Scheme C.

To secure a 7$\beta$-alkanoyloxy-6$\beta$-hydrazinocarbonyloxylabdane 21 wherein $R_5$ is as hereinbeforedescribed, a 6$\beta$-hydroxy-7$\beta$-hydrazinocarboxylabdane-1$\alpha$,9$\alpha$-dialkylformamide acetal 7 wherein $R_1$ and $R_9$ taken together form a group of the formula CHNR$_2$R$_3$ wherein $R_2$ and $R_3$ are alkyl, $R_5$ is alkyl and $R_8$ is hydrogen may be N-acylated to 6$\beta$-N-alkanoylhydrazinocarbonyloxy-7$\beta$-hydroxylabdane 19 wherein $R_{12}$ is alkyl, which in turn may be O-acylated to 7$\beta$-alkanoyloxylabdane 20 wherein $R_{22}$ is alkyl and hydrolyzed to 7$\beta$-alkanoyloxy-6$\beta$-hydrazinocarbonyloxylabdane 21 wherein $R_5$ is alkyl. The N-acylation may be accomplished by treatment of 7 with carboxylic acid anhydride 25 neat or in a suitable solvent. The O-acylation may be achieved by contacting a 7$\beta$-hydroxylabdane 19 with anhydride 26 or mixed anhydride 27 wherein $R_{22}$ and $R_{25}$ are as above in the presence of a substituted aminopyridine, for example, 4-N,N-dimethylaminopyridine, in an appropriate solvent, if necessary. The hydrolysis may be effected by contacting a N-alknoylhydrazinocarbonyloxylabdane-dialkylformamide acetal 20 with aqueous alkanol, for example, aqueous methanol, followed by treatment with a dilute base, for example, dilute potassium hydroxide solution, if required. See Reaction Scheme D.

To gain entry into the 6β-alkanoyloxy-7β-hydrazinocarbonyloxylabdane series, i.e., to prepare a 6β-alkanoyloxy-7β-hydrazinocarbonyloxylabdane 24 wherein $R_5$, $R_8$, and $R_{22}$ are as above, a 6β-alkanoyloxy-7β-hydroxylabdane-1α,9α-dialkylformamide acetal 22 wherein $R_1$ and $R_9$ together form a group of the formula $CHNR_2R_3$ wherein $R_2$ and $R_3$ are alkyl and $R_{22}$ is alkyl, the preparation of which is described in U.S. Pat. No. 4,639,443, issued Jan. 27, 1987, may be acylated to a 6β-alkanoyloxy-7β-hydrazinocarbonyloxylabdane 23 wherein $R_1$, $R_5$, $R_8$, and $R_{22}$ are as hereinbeforedescribed and hydrolyzed to a 6β-alkanoyloxy-1α,9α-dihydroxy-7β-hydrazinocarbonyloxylabdane 24 wherein $R_5$, $R_8$ and $R_{22}$ are as before. The acylation may be conducted by contacting hydroxy labdane 22 with phosgene or a quaternized 1,1'-carbonyldiimidazole such as, for example a 1,1'-carbonyldiimidazole 3-methyl or 3-allyl quaternary halide, ie.., chloride, bromide or iodide, in the presence of a trialkyamine, e.g., triethylamine, and a N-N-dialkylaminopyridine, e.g., 4-(N,N-dimethyl)aminopyridine, in a suitable solvent, if necessary, followed by a hydrazine 11. The hydrolysis may be achieved as before by contacting a 6β-alkanoyloxy-7β-hydrazinocarbonyloxylabdane-1α,9α-dialkylformamide acetal 23 with an aqueous alkanol, e.g., aqueous methanol, to provide a 6β-alkanoyloxy-1α,9α-dihydroxy-7β-hydrazinocarbonyloxylabdane 24 wherein $R_5$, $R_8$, and $R_{22}$ are as above. See Reactin Scheme E.

The hydrazinocarbonyloxylabdanes of the present invention are useful in the treatment of cardiac failure by virtue of their ability to elicit a positive inotropic effect as determined in the isolated guinea pig atria contractile force assay. The electrically-driven guinea pig left atrium assay is performed as follows:

Male guinea pigs weighing 200–300 grams are stunned with a blow to the back of the head. The heart is rapidly removed and placed in a petri dish containing Krebs solution. The ventricle is separated from the atria, the atria are sectioned into the right and left atria, and double-O silk ligatures are tied to the apex of the left atrium. The atrium is fixed to a pair of platinum plate electrodes and suspended in a 20-ml tissue bath containing Kreb's solution aerated with 95% oxygen-5% carbon dioxide at 37° C. One end of the atrium is fixed to a hook in the electrode and the other end is connected to a Grass FTO3 force displacement transducer. Resting tension and stabilization time are the same as described above. The atrium is stimulated at 3 Hz, 0.5 msec duration at supramaximal voltage (constant current) via a grass S88 stimulator and constant current unit. Force of contraction is continuously displaced on a Gould recorder. Test drug is prepared as in section A and is added to the tissue baths in the same fashion. Change in contractile force from baseline is determined for each concentration, and the change in contractile force (g) is plotted against accumulated drug concentration (μg/ml). The activity of the test drug, i.e., the increase in contractile force (g) from the stabilized force expressed as the percentage change at a given concentration is determined graphically, as is the $ED_{50}$-value, i.e., the extrapolated dose (μg/ml) which increases the contractile force by 50% over the stabilized rate.

Results obtained in this assay for representative hydrazinocarbonyloxylabdanes and a reference compound are presented in the Table.

TABLE

| COMPOUND | CONC (μg/ml) | INOTROPIC ACTIVITY CHANGE (%) OF CONTRACTILE FORCE (g) |
|---|---|---|
| 8,13-epoxy-7β-[(1-methylhydrazino)-carbonyloxy]-1α,6β,9α-trihydroxylabd-14-en-11-one | 0.62 | 50 |
| 8,13-epoxy-7β-[(1-oxo-propylhydrazinocarbonyloxy]-1α,6β,9α-trihydroxylabd-14-en-11-one | 0.28[1] | 50 |
| milrinone | 0.34[1] | 50 |

[1]extrapolated $ED_{50}$-value.

Cardiac failure treatment is achieved when the present hydrazinocarbonyloxylabdanes are administered to a subject requiring such treatment as an effective oral, parenteral or intravenous dose of from about 0.01 to 100 mg/kg of body weight per day. A particularly effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosage set forth herein are exemplary only and that they do not, to any extent, limit the scope or practice of the invention.

Compounds of the present invention are also useful for the treatment of hypertension, bronchial asthma, glaucoma and psoriasis.

Compounds of the present invention include:

(1)  8,13-epoxy-7β-hydrazinocarbonyloxy-1α,6β,9α-trihydroxylabd-14-en-11-one-1,9-sulfite;

(2)  8,13-epoxy-7β-hydrazinocarbonyloxy-1α,6β,9α-trihydroxylabd-14-en-11-one-1,9-carbonate;

(3)  8,13-epoxy-6β-[(1-morpholinoaminocarbonyloxy]-1α,7β,9α-trihydroxylabd-14-en-11-one;

(4)  8,13-epoxy-6β-[(1-thiomorpholinoamino)carbonyloxy]-1α,7β,9α-trihydroxylabd-14-en-11-one;

(5)  8,13-epoxy-6β-[(4-hydroxypiperidin-1-ylamino)carbonyloxy]-1α,7β,9α-trihydroxylabd-14-en-11-one;

(6)  8,13-epoxy-7β-[2-(1-hydroxyethylethyliden-1-yl)hydrazinocarbonyloxy]-1α,6β,9α-trihydroxy-14-en-11-one;

(7)  8,13-epoxy-7β-[2-(1-methylpropyliden-1-yl)hydrazinocarbonyloxy]-1α,6β,9α-trihydroxy-14-en-11-one;

(8)  8,13-epoxy-6β-[2-(1-tetrahydrofuran-2-yl-ethyliden-1-yl)hydrazinocarbonyloxy]-1α,7β,9α-trihydroxy-14-en-11-one;

(9)  8,13-epoxy-7β-[2-(tetrahydrofuryliden-2-yl)hydrazinocarbonyloxy]-1α,6β,9α-trihydroxylabd-14-en-11-one;

(10)  8,13-epoxy-7β-[2-(4-hydroxycyclohexyliden-1-yl)hydrazinocarbonyloxy]-1α,6β-9α-trihydroxylabd-14-en-11-one;

(11) 1α,9α-dihydroxy-8,13-epoxy-7β-formyloxy-6β-[(1-piperidinoamino)carbonyloxy]labd-14-en-11-one;

(12)  7β-acetoxy-1α,9α-dihydroxy-6β-[(1-piperidionoamino)carbonyloxy]labd-14-en-11-one;

(13) 1α,9α-dihydroxy-7β-[(2,2-dimethylhydrazino)carbonyloxy]8,13-epoxy-6β-formyloxylabd-14-en-11-one;

(14) 6β-actoxy-1α,9α-dihydroxy-7β-[(2,2-dimethylhydrazino)carbonylox]-8,13-epoxylabd-14-en-11-one;

(15) 7β-[2-(3-dimethylaminopropyl-2-methylhydrazino)carbonyloxy]-8,13-epoxy-1α,6β,9α-trihydroxylabd-14-en-11-one; and

(16) 6β-[2-(4-dimethylaminobutyl)hydrazinocarbonylox]-8,13-epoxy-1α,7β,9α-trihydroxylabd-14-en-11-one.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 5% of the weight thereof. The amount of active compound in such compositions is such that a suitable dosage will be obtained. Preferred compositions and preparations according to the present inventions are prepared so that a parenteral dosage unit contains between 0.001 to 10 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citates or phosphates and agents for the adjustment of tonicity such as sodium chloride or dextrose. The parenteral preparations can be enclosed in disposable syringes or multiple dose vials made of glass or plastic.

The following examples are for illustrative purposes only and are not to be construed as limiting the invention. All temperatures are given in degrees Centigrade.

EXAMPLE 1

7β-[(2,2-Dimethylhydrazino)carbonyloxy]-8,13-epoxy-1α,6β,9α-trihydroxylabd-14-en-11-one-1,9-dimethylformamide acetal To a stirred solution of 3.0 g of 8,13-epoxy-1α,6β,7β,-9α-tetrahydroxylabd-14-en-11-one-1,9-dimethylformamide acetal in 60 ml of dry ethyl acetate was added 1.22 g of 1,1'-carbonyldiimidazle. The mixture was stirred under nitrogen for 16 hr. To the solution was added 60 ml of 1,1'-dimethylhydrazine. The mixture was stirred at room temperature under nitrogen for 24 hr. The solution was diluted with ethyl acetate, washed with water and back extracted with ethyl acetate. The combined ethyl acetate solutions were washed with water, saturated sodium chloride solution, dried over anhydrous sodium sulfate, filtered and evaporated. The residue was dissolved in a minimum volume of 2/1 ethyl acetate/hexanes and flash chromatographed on silica gel. Concentration of the appropriate fractions provided an oil which crystallized on standing to give 0.74 g (20%) of product, mp 132°–136°.

| ANALYSIS | | | |
|---|---|---|---|
| Calculated for $C_{26}H_{43}N_3O_7$ | 61.27% C | 8.50% H | 8.25% N |
| Found | 61.03% C | 8.57% H | 8.21% N |

EXAMPLE 2

7β-[(2,2-Dimethylhydrazino)carbonyloxy]-8,13-epoxy-1α,6β,9α-trihydroxylabd-14-en-11-one A solution of 0.35 g of 7β-[2,2-dimethylhydrazino)-carbonyloxy-8,13-epoxy-1α,6β,9α-trihydroxylabd-14-en-11-one-1,9-dimethylformamide acetal in 10 ml of water/methanol (1/3) was stirred at room temperature overnight and at 60° for 48 hr. The solution was diluted with ethyl acetate, washed three times with water, once with saturated sodium chloride solution, dried over anhydrous sodium sulfate and filtered. The filtrate was evaporated and the residue was dissolved in a minimum volume of 30% acetone/hexane and flash chromatographed on silica gel/eluent: 30% acetone/hexane.

Concentration of the appropriate fractions provided 0.143 g (45.9%) of product, mp 105°–118°.

| ANALYSIS | | | |
|---|---|---|---|
| Calculated for $C_{23}H_{38}N_2O_7$ | 60.77% C | 8.43% H | 6.16% N |
| Found | 60.80% C | 8.66% H | 5.96% N |

EXAMPLE 3

7β-[(2-Methylhydrazino)carbonyloxy]-8,13-epoxy-1α,6β,9α-trihydroxylabd-14-en-11-one-1,9-dimethylformamide acetal A solution of 3.0 g of 8,13-epoxy-1α,6β,7β,9α-tetrahydroxylabd-14-en-11-one-1,9-dimethylformamide acetal, 60 ml of ethyl acetate, and 1.38 g of 1,1'-carbonyldiimidazole was stirred at room temperature for 16 hr under nitrogen. To the reaction mixture was added an additional 0.2 g of 1,1'-carbonyldiimidazole. The reaction was stirred for 2 hr at room temperature. To the solution was added 60 ml of N-methylhydrazine. The mixture was stirred for 16 hr at room temperature. The solution was diluted with ethyl acetate and water, extracted twice with ethyl acetate, washed three times with water, once with saturated sodium chloride solution and dried over anhydrous sodium sulfate. The suspension was filtered and the filtrate was concentrated. The residue was dissolved in a minimum volume of 30% acetone/hexanes and flash chromatographed on silica gel to provide two pure products. The fractions containing the minor, slower eluting product were combined and concentrated to provide, after drying at 110° (1 mm), 317 mg (9.0%) of product, as an oil.

| ANALYSIS | | | |
|---|---|---|---|
| Calculated for $C_{25}H_{41}N_3O_7$ | 60.58% C | 8.34% H | 8.48% N |
| Found | 60.51% C | 8.20% H | 8.25% N |

EXAMPLE 4

8,13-Epoxy-7β-hydrazinocarbonyloxy-1α,6β,9α-trihydroxylabd-14-en-11-one-1,9-dimethylformamide acetal To a stirred solution of 3.09 g of 8,13-epoxy-1α,6β,9α-tetrahydroxylabd-14-en-11-one-1,9-dimethylformamide acetal in 60 ml of dry tetrahydrofuran was added 1.38 g of 1,1'-carbonyldiimidazole. To the solution was added an additional 0.2 g of 1,1'-carbonyldiimidazole and stirring was continued overnight at room temperature. To the solution was added 60 ml of anhydrous hydrazine. The mixture was stirred for 8 hr, poured into ice/water, washed twice with water and once with saturated sodium chloride solution. The solution was dried over anhydrous sodium sulfate, filtered and concentrated. Crystallization of the residue from ethyl acetate provided 2.24 g (65.6%) of product, mp 204°–209°.

| ANALYSIS | | | |
|---|---|---|---|
| Calculated for $C_{24}H_{39}N_3O_7$ | 59.84% C | 8.16% H | 8.73% N |
| Found | 59.88% C | 8.26% H | 8.56% N |

EXAMPLE 5

8,13-Epoxy-7β-hydrazinocarbonyloxy-1α,6β,9α-trihydroxylabd-14-en-11-one

To a stirred solution of 5.0 g of 8,13-epoxy-1α,6β,7β,9α-tetrahydroxylabd-14-en-11-one-1,9-dimethylformamide acetal in 100 ml of methylene chloride was added 2.3 g of 1,1'-carbonyldiimidazole and the mixture was allowed to stir overnight at room temperature under a nitrogen atmosphere. Anhydrous hydrazine (1.9 ml) in 15 ml of methylene chloride was added to the reaction mixture and the resulting solution was stirred overnight. The solvent was evaporated and the residue was flash chromatographed on silica gel. The column was eluted with 5% methanol/methylene chloride. The appropriate fractions were combined, the solvent was evaporated, and the residue was crystallized from hexane/ether to give 710 mg (14.2%) of product, mp 110°–115°.

| ANALYSIS | | | |
|---|---|---|---|
| Calculated for $C_{21}H_{34}N_2O_7$ | 59.12% C | 8.05% H | 6.58% N |
| Found | 59.13% C | 8.21% H | 6.71% N |

EXAMPLE 6

8,13-Epoxy-6β-[(1-piperidinoamino)carbonyloxy]-1α,7β,9α-trihydroxylabd-14-en-11-one-1,9-dimethylformamide acetal To a stirred solution of 4.0 g of 8,13-epoxy-1α,6β,7β,9α-tetrahydroxylabd-14-en-11-one-1,9-dimethylformamide acetal in 80 ml of methylene chloride was added 1.84 g of 1,1'-carbonyldiimidazole, followed by 1.16 g of triethylamine. The mixture was allowed to stir overnight under a nitrogen atmosphere. 1-Aminopiperidine (4.7 g) was added to the reaction mixture and the mixture was stirred under nitrogen. After three days, the reaction mixture was evaporated under reduced pressure and the residue was stirred neat overnight. The residue was diluted with methylene chloride and washed with 0.01N hydrochloric acid until the washings were acidic. The layers were separated, the methylene chloride layer was dried over anhydrous sodium sulfate, filtered and the filtrate was evaporated. The residue was flash chromatographed on a column of silica gel, eluted with hexane/acetone (2:1). The appropriate fractions were collected and the solvent was removed to give 3.2 g (62%) of product.

| ANALYSIS | | | |
|---|---|---|---|
| Calculated for $C_{29}H_{47}N_3O_7$ | 63.35% C | 8.63% H | 7.64% N |
| Found | 63.34% C | 8.60% H | 7.50% N |

EXAMPLE 7

8,13-Epoxy-6β-[(1-piperidinoamino)carbonyloxy])-1α,7β,9α-trihydroxylabd-14-en-11-one 8,13-Epoxy-6-[1-piperidinoamino)carbonyloxy-1α,7β,9α-trihydroxylabd-14-en-11-one-1,9-dimethylformamide acetal (1.2 g) was dissolved in 24 ml of a methanol/acetic acid/water (10/8/2) solution. The mixture was stirred at room temperature for 24 hr, neutralized with saturated sodium bicarbonate solution and extracted with methylene chloride (3×50 ml). The methylene chloride extracts were dried over anhydrous sodium sulfate, filtered and the filtrate was evaporated under reduced pressure. The residue was chromatographed on silica gel. The column was eluted with 5% methanol/methylene chloride, the appropriate fractions were collected and the solvent was evaporated to give 0.59 g (54%) of product, mp 232°.

| ANALYSIS | | | |
|---|---|---|---|
| Calculated for $C_{26}H_{42}N_2O_7$ | 63.12% C | 8.57% H | 5.66% N |
| Found | 62.96% C | 8.54% H | 5.76% N |

EXAMPLE 8

8,13-Epoxy-7β-[1-methyl-2-(1-methylethyliden-1-yl)]hydrazinocarbonyloxy-1α,6β,9α-trihydroxylabd-14-en-11-one-1,9-dimethylformamide acetal A solution of 3.0 g of 8,13-epoxy-1α,6β,7β,9α-tetrahydroxylabd-14-en-11-one-1,9-dimethyformamide acetal, 60 ml of ethyl acetate and 1.38 g of 1,1'-carbonyldiimidazole was stirred at room temperature for 16 hr under nitrogen. To the reaction mixture was added an additional 0.1 g of 1,1'-carbonyldiimidazole and the reaction mixture was stirred for 2 hr at room temperature. To the solution was added 60 ml of N-methylhydrazine and the mixture was stirred 16 hr at room temperature. The solution was diluted with ethyl acetate/water, extracted twice with ethyl acetate, washed three times with water, once with saturated sodium chloride solution, dried over anhydrous sodium sulfate and filtered. The filtrate was evaporated. The residue was dissolved in a minimum volume of 30% acetone/hexane and flash chromatographed on silica gel. Fractions containing the major, faster eluting material were combined and concentrated to provide 1.56 g (41%) of product as an oil.

| Calculated for $C_{28}H_{45}N_3O_7$ | 62.78% C | 8.47% H | 7.85% N |
|---|---|---|---|
| Found | 63.36% C | 8.33% H | 7.78% N |

EXAMPLE 9

8,13-Epoxy-7β-[(1-methylhydrazino)carbonyloxy]-1α,6β,9α-trihydroxylabd-14-en-11-one A solution of 1.35 g of 8,13-epoxy-7β-[1-methyl-2-(1-methylethylidene-1-yl)hydrazinocarbonyloxy]-1α,6β,9α-trihydroxylabd-14-en-11-one in 40 ml of water/methanol (1/3) was stirred at 50°-60° for 48 hr under nitrogen. The solution was diluted with ethyl acetate, washed three times with water, once with saturated sodium chloride solution, dried over anhydrous sodium sulfate and filtered. The filtrate was concentrated. The residue which crystallized on standing was recrystallized from chloroform. The crystalline material was dissolved in ethyl acetate and flash chromatographed on silica gel. The column was eluted with 60% ethyl acetate hexane, followed by pure ethyl acetate. Concentration of the appropriate fractions provided 0.31 g (28%) of product, mp 235°-237°. Evaporation of the chloroform extract furnished an additional 0.29 g of product to give a total yield of 0.60 g (54%).

| ANALYSIS | | | |
|---|---|---|---|
| Calculated for $C_{22}H_{36}N_2O_7$ | 59.98% C | 8.24% H | 6.36% N |
| Found | 59.98% C | 8.07% H | 6.13% N |

EXAMPLE 10

8,13-Epoxy-7β-[1-methyl-2-(1-methylethyliden-1-yl)hydrazinocarbonyloxy]-1α,6β,9α-trihydroxylabd-14-en-11-one A solution of 1.35 g of 8,13-epoxy-7β-[1-methyl-2-(1-methylethyliden-1-yl)]hydrazinocarbonyloxy-1α,6β,9α-trihydroxylabd-14-en-11-one-1α,9α-dimethylformamide acetal in 40 ml of water/methanol (1/3) was stirred at 50°-60° for 48 hr under nitrogen. The solution was diluted with ethyl acetate, washed three times with water, once with saturated sodium chloride solution, filtered and concentrated. The residue was dissolved in chloroform. The suspension was filtered and the filtrate concentrated. The residue was dissolved in acetone and stirred for 15 min. The solution was then concentrated, the residue was dissolved in a minimum volume of 25% acetone/hexane and flash chromatographed on silica gel. Concentration of the appropriate fractions provided an oil which crystallized on standing. The solid was triturated with cyclohexane/ethyl acetate to provide 0.186 g (43.6%) of product, mp 184°-185°.

| ANALYSIS | | | |
|---|---|---|---|
| Calculated for $C_{25}H_{40}N_2O_7$ | 62.48% C | 8.39% H | 5.83% N |
| Found | 62.12% C | 8.03% H | 5.93% N |

EXAMPLE 11

8,13-Epoxy-7β-[2-(cyclohexyliden-1-yl)hydrazinocarbonyloxy]-1α,6β,9α-trihydroxylabd-14-en-11-one A solution of 2.1 g of 8,13-epoxy-7β-hydrazinocarbonyloxy-1α,6β,9α-trihydroxylabd-14-en-11-one in 50 ml of 15/3/2 hexane/ethyl acetate/cyclohexanone was filtered through 350 g of silica gel (230-400 mesh) and eluted with hexane/ethyl acetate. The fractions containing the major product were combined and concentrated under high vacuum. The residue was dissolved in 40% ethyl acetate/hexane and flash chromatographed on 350 g of silica gel, eluting with the same solvent. Concentration of the appropriate fractions followed by recrystallization from ethyl acetate gave 0.532 g (20.7%) of product, mp 186°-188°.

| ANALYSIS | | | |
|---|---|---|---|
| Calculated for $C_{27}H_{42}N_2O_7$ | 64.01% C | 8.36% H | 5.33% N |
| Found | 63.67% C | 8.85% H | 5.61% N |

EXAMPLE 12

8,13-Epoxy-7α-[(1-oxopropylhydrazino)carbonyloxy]-1α,6β,9α-trihydroxylabd-14-en-11-one A stirred solution of 0.73 g of 8,13-epoxy-7β-hydrazinocarbonyloxy-1α,6β,9α-trihydroxylabd-14-en-11-one in 30 ml of dry dichloromethane was treated dropwise with 0.27 g of propionic anhydride in 1 ml of dry dichloromethane. The solution was stirred at room temperature for 1 hr, poured onto ice/water/dichloromethane, washed twice with water, dried over anhydrous sodium sulfate and filtered. The filtrate was evaporated. The residue was dissolved in a minimum volume of ethyl acetate and flash chromatographed on silica gel with 1/1-ethyl acetate/hexane as the eluent. The appropriate fractions were combined and concentrated to provide 0.58 g (71%) of product, mp 154°–170°.

| ANALYSIS | | | |
|---|---|---|---|
| Calculated for $C_{24}H_{38}N_2O_8$ | 59.78% C | 7.94% H | 5.81% N |
| Found | 59.27% C | 8.19% H | 6.14% N |

EXAMPLE 13

8,13-Epoxy-7β-[2-(1-methylethyliden-1-yl)hydrazinocarbonyloxy]-1α,6β,9α-trihydroxylabd-14-en-11-one-1,9-dimethylformamide acetal To a stirred solution of 5.0 g of 8,13-epoxy-1α,6β,7β,-9α-tetrahydroxylabd-14-en-11-one,1,9-dimethylformamide acetal in 100 ml of methylene chloride was added 2.3 g of 1,1'-carbonyldiimidazole. The mixture was stirred at room temperature under nitrogen for 18 hr. Hydrazine (1.9 g) was added to the reaction mixture, and the mixture was stirred overnight. The solution was concentrated and the residue was chromatographed on silica gel, eluting successively with 5% methanol/methylene chloride and then hexane/acetone (2/1). The appropriate fractions were collected and the solvent was evaporated to give 3.1 g (50%) of product, mp 155°–157°.

| ANALYSIS | | | |
|---|---|---|---|
| Calculated for $C_{27}H_{43}N_3O_7$ | 62.15% C | 8.32% H | 8.05% N |
| Found | 62.25% C | 8.32% H | 7.88% N |

EXAMPLE 14

8,13-Epoxy-6β-(hydrazinocarbonyloxy)-1α,7β,9α-trihydroxylabd-14-en-11-one-1,9-dimethylformamide acetal To a stirred solution of 3.0 g of 8,13-epoxy-1α,6β,7β,-9α-tetrahydroxylabd-14-en-11-one-1,9-dimethylformamide acetal in 60 ml of methylene chloride was added 1.38 g of 1,1'-carbonyldiimidazole, followed by 1.2 ml of triethylamine. The mixture was stirred for 48 hrs at room temperature under a nitrogen atmosphere. Hydrazine (1.1 g) was added and the mixture was stirred for an additional 24 hrs. The reaction mixture was washed with 0.01N hydrochloric acid until the washings were neutral. The organic portion was dried over anhydrous sodium sulfate and the solvent removed. The residue was recrystallized from hexane/ether to give 2.4 g (75%) of product, mp 143°.

| ANALYSIS | | | |
|---|---|---|---|
| Calculated for $C_{24}H_{39}N_3O_7$ | 59.84% C | 8.18% H | 8.72% N |
| Found | 59.02% C | 8.09% H | 8.55% N |

EXAMPLE 15

8,13-Epoxy-7β-[2-(1-methylethyliden-1-yl)hydrazinocarbonyloxy]-1α,6β,9α-trihydroxylabd-14-en-11-one A solution of 2.0 g of 8,13-epoxy-7β-[2-(1-methylethyliden-1-yl)hydrazinocarbonyloxy]-1α,6β,-9α-trihydroxylabd-14-en-11-one-1,9-dimethylformamide acetal, 50 ml of methanol and 16 ml of water was stirred at 55° overnight. The solution was diluted with ethyl acetate, the ethyl acetate layer was washed with water, saturated sodium chloride solution, filtered and concentrated. The residue was dissolved in a minimum volume of 2:1 hexane:acetone and flashed chromatographed on silia gel. Concentration of the appropriate fractions followed by crystallization of the residue with hexane:acetone provided 820 mg (46%) of product, mp 143°–145°. The analytical sample, prepared by additional flash chromatographic purification followed by crystallization with hexane:acetone and then hexane:ethyl acetate, had mp 184°–185°.

| ANALYSIS | | | |
|---|---|---|---|
| Calculated for $C_{24}H_{38}N_2O_7$ | 61.77% C | 8.22% H | 6.00% N |
| Found | 60.38% C | 8.52% H | 5.99% N |

REACTION SCHEME A

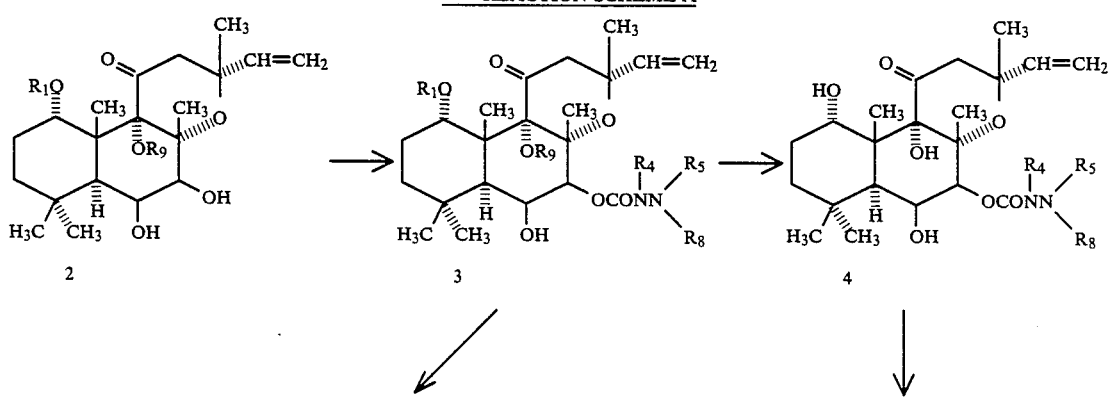

-continued
REACTION SCHEME A
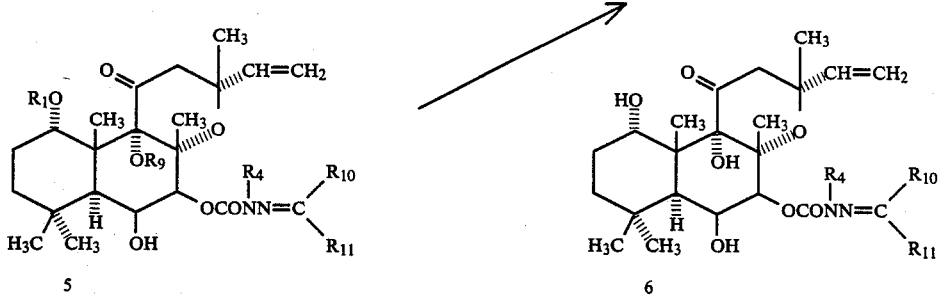
wherein $R_1$, $R_4$, $R_5$, $R_8$, $R_9$, $R_{10}$ and $R_{11}$ are as hereinbefore defined
REACTION SCHEME B
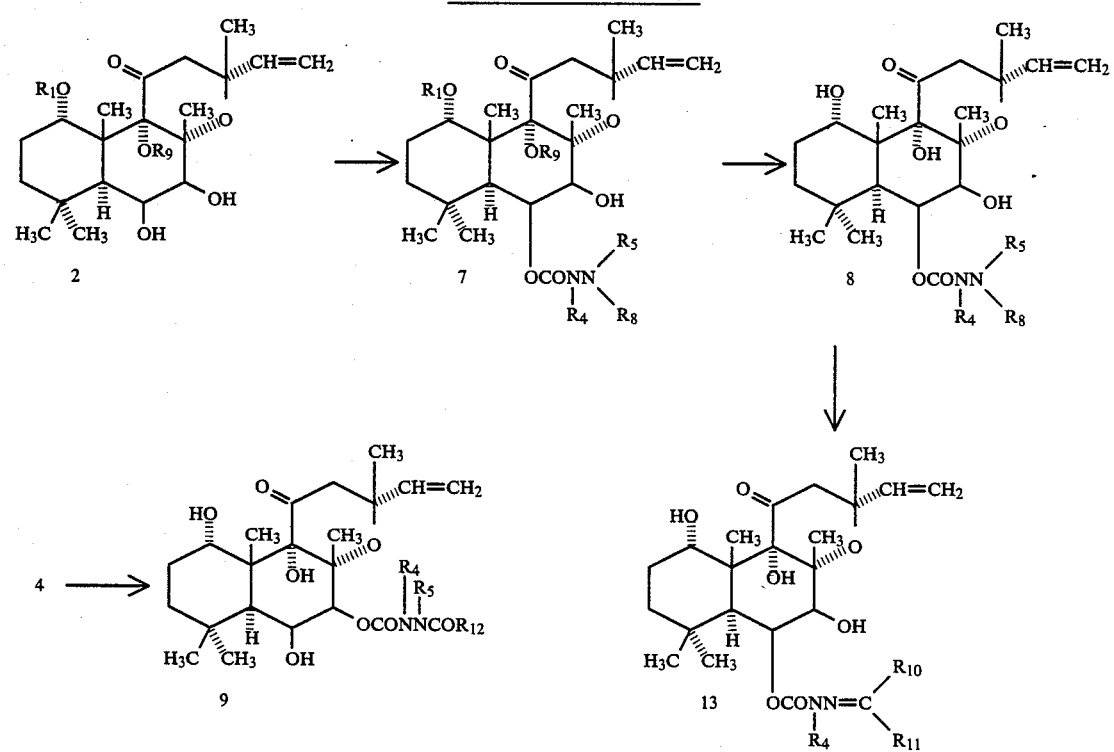
wherein $R_1$, $R_4$, $R_5$, $R_9$, $R_{10}$, $R_{11}$ and $R_{12}$ are as herinbefore defined.
REACTION SCHEME C
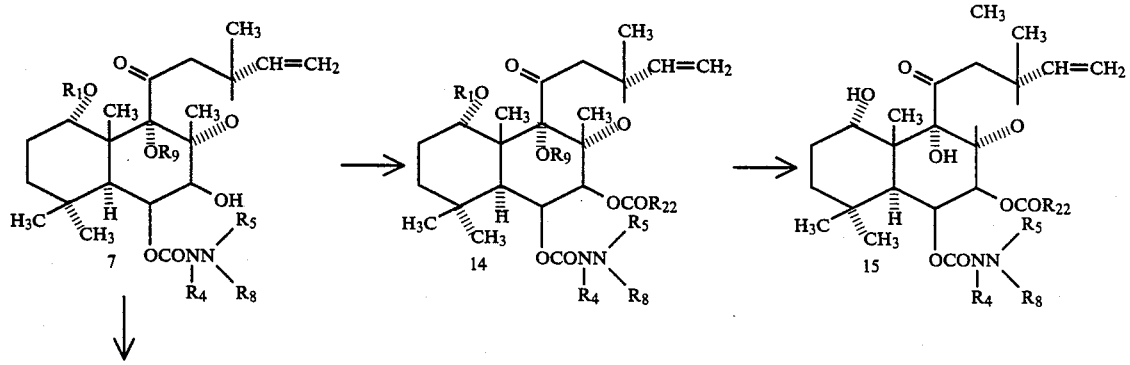

-continued
REACTION SCHEME C
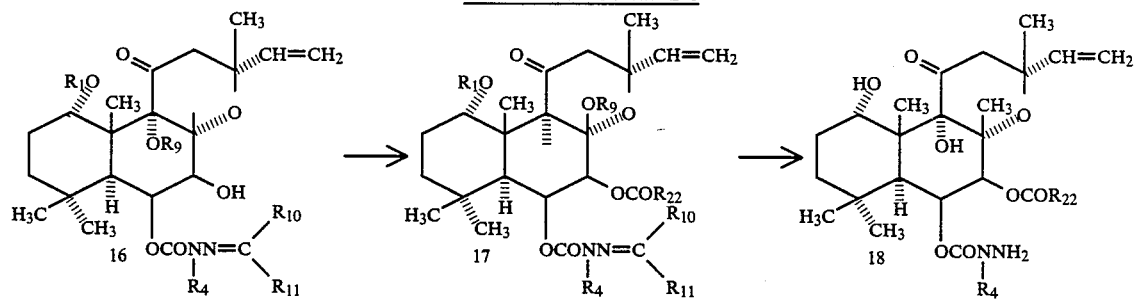
wherein $R_1$, $R_4$, $R_5$, $R_8$, $R_9$, $R_{10}$, $R_{11}$ and $R_{22}$ are as hereinbefore described.
REACTION SCHEME D
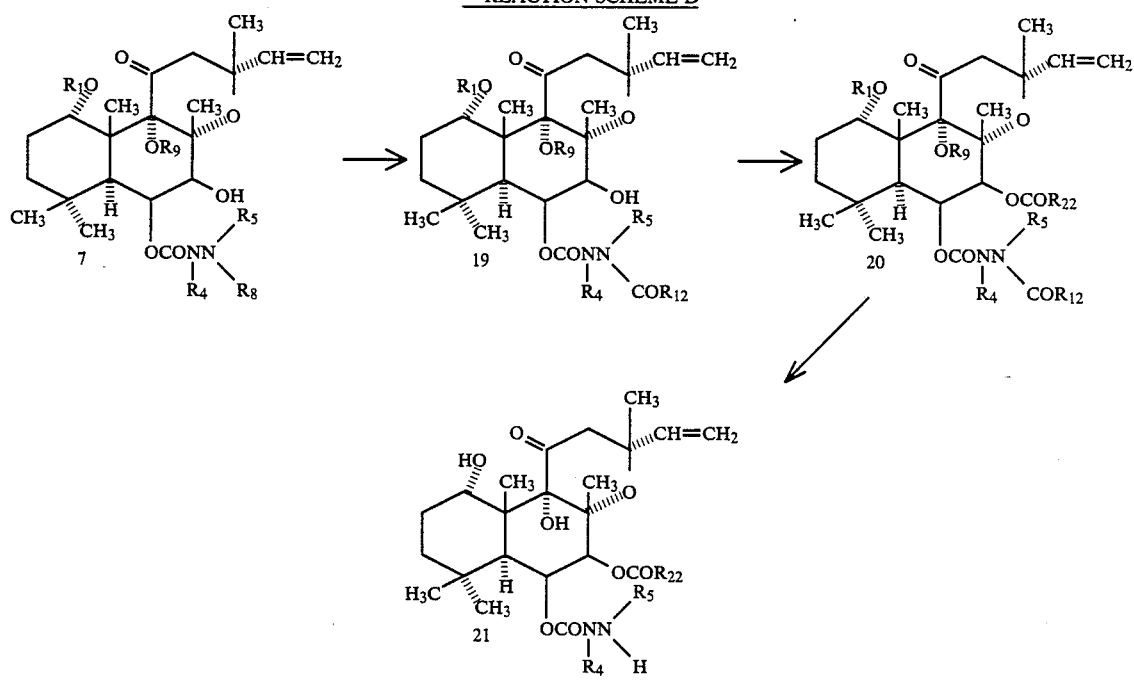
wherein $R_1$, $R_4$, $R_5$, $R_8$, $R_9$, $R_{12}$ and $R_{22}$ are as hereinbefore defined.
REACTION SCHEME E
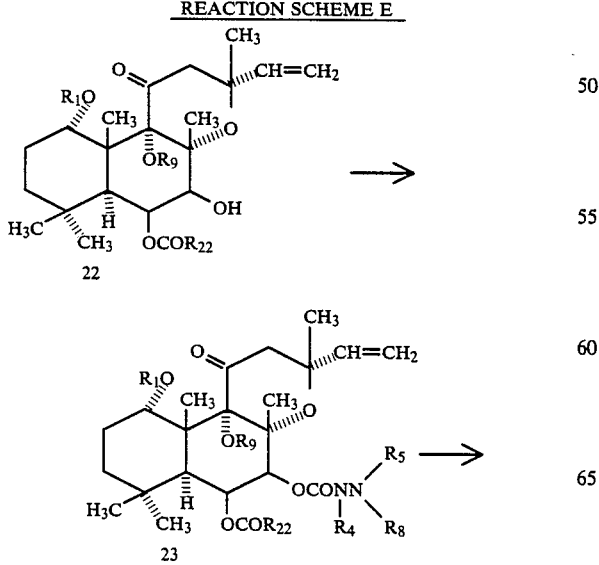
-continued
REACTION SCHEME E
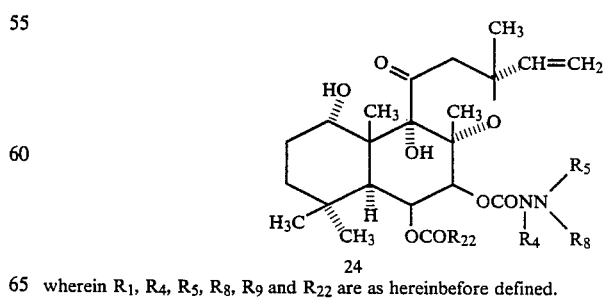
wherein $R_1$, $R_4$, $R_5$, $R_8$, $R_9$ and $R_{22}$ are as hereinbefore defined.
We claim:
1. A compound of the formula

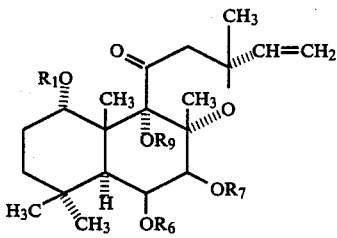

wherein:
(a) $R_1$ and $R_9$ are hydrogen;
(b) $R_1$ and $R_9$ taken together form a group of the formula CO, a group of the formula SO or a group of the formula $CHNR_2R_3$ wherein $R_2$ and $R_3$ are loweralkyl;
(c) $R_6$ and $R_7$ are independently hydrogen, a group of the formula $COR_{22}$ wherein $R_{22}$ is hydrogen or loweralkyl, or a group of the formula $CONR_4Z$ wherein $R_4$ is hydrogen or loweralkyl and Z is a group of the formula $NR_5R_8$ or a group of the formula $N=CR_{10}R_{11}$ wherein $R_5$ and $R_8$ are independently hydrogen, loweralkyl or a group of the formula $COR_{12}$ wherein $R_{12}$ is loweralkyl or a group of the formula $(CH_2)_nNR_{23}R_{24}$ wherein $R_{23}$ and $R_{24}$ are loweralkyl and n is an integer from 2 to 5; $R_5$ and $R_8$ taken together with the nitrogen atom to which they are attached form a group of the formula

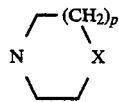

wherein X is O, S or a group of the formula $CHR_{13}$ wherein $R_{13}$ is hydrogen, loweralkyl or a group of the formula $OR_{14}$ wherein $R_{14}$ is hydrogen, loweralkyl or a group of the formula $COR_{15}$ wherein $R_{15}$ is loweralkyl and p is 0 or 1; $R_{10}$ is hydrogen, loweralkyl or hydroxyloweralkyl; $R_{11}$ is loweralkyl, loweralkenyl, hydroxyloweralkyl, a group of the formula

or a group of the formula

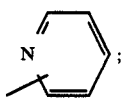

and $R_{10}$ and $R_{11}$ taken together with the carbon atom to which they are attached form a group of the formula

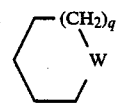

wherein W is O, S, a group of the formula $NR_{19}$ wherein $R_{19}$ is hydrogen or loweralkyl or a group of the formula $CHR_{16}$ wherein $R_{16}$ is hydrogen, loweralkyl or a group of the formula $OR_{17}$ wherein $R_{17}$ is hydrogen, loweralkyl or a group of the formula $COR_{18}$, wherein $R_{18}$ is loweralkyl and q is 0 or 1, with the proviso that either $R_6$ or $R_7$ is a group of the formula $CONR_4Z$ wherein $R_4$ and Z are as above; or an optical or geometrical isomer thereof, or a pharmaceutically acceptable salt thereof.

2. A compound according to claim 1 wherein $R_1$ and $R_9$ are hydrogen and Z is a group of the formula $NR_5R_8$.

3. A compound according to claim 1 wherein $R_1$ and $R_9$ taken together form a group of the formula $CHNR_2R_3$ and Z is $NR_5R_8$.

4. A compound according to claim 1 wherein $R_1$ and $R_9$ are hydrogen and Z is $N=CR_{10}R_{11}$.

5. A compound according to claim 1 wherein $R_1$ and $R_9$ taken together form a group of the formula $CHNR_2R_3$ and Z is $N=CR_{10}R_{11}$.

6. The compound according to claim 2 which is 7β-[(2,2-dimethylhydrazino)carbonyloxy]-8,13-epoxy-1α,6β,9α-trihydroxylabd-14-en-11-one.

7. The compound according to claim 2 which is 8,13-epoxy-7β-hydrazinocarbonyloxy-1α,6β,9α-trihydroxylabd-14-en-11-one.

8. The compound according to claim 2 which is 8,13-epoxy-6β-[(1-piperidinoamino)carbonyloxy]-1α,7β,9α-trihydroxylabd-14-en-11-one.

9. The compound according to claim 2 which is 8,13-epoxy-7β-[(1-methylhydrazino)carbonyloxy]-1α,6β,9α-trihydroxylabd-14-en-11-one.

10. The compound according to claim 2 which is 8,13-epoxy-7β-[(1-oxopropylhydrazino)carbonyloxy]-1α,6β,9α-trihydroxylabad-14-en-11-one.

11. The compound according to claim 3 which is 7β-[(2,2-dimethylhydrazino)carbonyloxy]-8,13-epoxy-1α,6β,9α-trihydroxylabd-14-en-11-one-1,9-dimethylformamide acetal.

12. The compound according to claim 3 which is 7β-[(2-methylhydrazino)carbonyloxy]-8,13-epoxy-1α,6β,9α-trihydroxylabd-14-en-11-one-1,9-dimethylformamide acetal.

13. The compound according to claim 3 which is 8,13-epoxy-7β-hydrazinocarbonyloxy-1α,6β,9α-trihydroxylabd-14-en-11-one-1,9-dimethylformamide acetal.

14. The compound according to claim 3 which is 8,13-epoxy-6β-[1-piperidinoamino)carbonyloxy]-1α,7β,9α-trihydroxylabd-14-en-11-one-1,9-dimethylformamide acetal.

15. The compound according to claim 4 which is 8,13-epoxy-7β-[1-methyl-2-(1-methylethyliden-1-yl)hydrazinocarbonyloxy]-1α,6β,9α-trihydroxylabd-14-en-11-one.

16. The compound according to claim 4 which is 8,13-epoxy-7β-[2-(cyclohexyliden-1-yl)hydrazinocarbonyloxy]-1α,6β,9α-trihydroxylabd-14-en-11-one.

17. The compound according to claim 4 which is 8,13-epoxy-7β-[2-(1-methylethyliden-1-yl)hydrazinocarbonyloxy]-1α,6β,9α-trihydroxylabd-14-en-11-one.

18. The compound according to claim 5 which is 8,13-epoxy-7β-[2-(1-methylethyliden-1-yl)hydrazinocarbonyloxy]-1α,6β,9α-trihydroxylabd-14-en-11-one-1,9-dimethylformamide acetal.

19. The compound according to claim 5 which is 8,13-epoxy-7β-[1-methyl-2-(1-methylethyliden-1-yl)hydrazinocarbonyloxy]-1α,6β,9α-trihydroxy-14-en-11-one,1-9-dimethylformamide acetal.

20. The compound according to claim 3 which is 8,13-epoxy-6β-hydrazinocarbonyloxy-1α,7β,9α-trihydroxylabd-14-en-11-one-1,9-dimethoxyformamide acetal.

21. A cardiac failure treating composition comprising an inert cardiac failure treating adjuvant and as the active ingredient, a cardiac failure treating effective amount of a compound of claim 1.

22. A method of treating cardiac failure comprising administering to a mammal requiring cardiac failure treatment, a cardiac failure treating effective amount of a compound of claim 1.

* * * * *